(12) United States Patent
Critz et al.

(10) Patent No.: US 6,629,612 B2
(45) Date of Patent: Oct. 7, 2003

(54) BIOLOGICAL FILTRATION STATION

(76) Inventors: Carl H. Critz, 24 Tea Tree Ct., Danville, CA (US) 94526; Joseph H. Hale, 14 Mayo Dr., Warren, RI (US) 02885

( * ) Notice: Subject to any disclaimer, the term of this patent is extended or adjusted under 35 U.S.C. 154(b) by 0 days.

(21) Appl. No.: 09/820,603

(22) Filed: Mar. 30, 2001

(65) Prior Publication Data

US 2002/0139743 A1 Oct. 3, 2002

(51) Int. Cl.[7] .......... B01D 24/00; B01D 29/00; B01D 35/00; B01L 11/00
(52) U.S. Cl. .......... 210/475; 210/473; 422/101; 422/102; 422/104; 436/174
(58) Field of Search .......... 210/238, 232, 210/248, 249, 475, 473; 422/101, 102, 99, 104; 436/174, 63, 176

(56) References Cited

U.S. PATENT DOCUMENTS

| | | |
|---|---|---|
| 618,996 A | 2/1899 | Riedel et al. |
| 2,533,815 A | 12/1950 | Kelly |
| 4,220,252 A | 9/1980 | Beall et al. |
| 4,321,139 A | 3/1982 | Auclair |
| 4,439,319 A | 3/1984 | Rock |
| 4,557,903 A | 12/1985 | McCormick |
| 4,752,347 A | 6/1988 | Rada |
| 4,801,553 A | 1/1989 | Owen et al. |
| 5,312,758 A | 5/1994 | Ahlqvist |
| 5,424,040 A | 6/1995 | Bjornsson |
| 5,427,742 A | 6/1995 | Holland |
| 5,532,168 A | 7/1996 | Marantz |
| 5,817,032 A | 10/1998 | Williamson, IV |

*Primary Examiner*—Joseph Drodge
*Assistant Examiner*—K S Menon
(74) *Attorney, Agent, or Firm*—John P. McGonagle

(57) ABSTRACT

A filtration station for capturing small to medium sized tissue fragments in fluid for histological processing. The filtration station allows tissue to be filtered onto foam in a cassette or into a biopsy bag with speed, excellent tissue recovery and convenient fixative collection for recycling or disposal. The present invention combines two normally separate filtration stations into one station for more convenient filtration of tissue into two widely used filter media while also reducing exposure to harmful vapors.

12 Claims, 4 Drawing Sheets

BIOLOGICAL FILTRATION STATION

BACKGROUND OF THE INVENTION

This invention relates to the general art of analysis of tissue samples, and in particular to obtaining, handling and processing small to medium sized tissue samples in fluid for histological processing.

Various disease processes, particularly tumors, require a histologic diagnosis. Cell types of a tumor are generally determined by a pathologist's examination of a histologic sample of the tumor. There are a number of devices that have been fashioned to actually perform the act of taking tissue samples. In many cases, these samples are very small and difficult to retrieve and process. The small tissue fragments originating from various biopsy procedures are generally rinsed into a specimen container with a preservative effluent, such as 10% formalin, to prevent loss of the sample, dehydration of the sample, and contamination of the sample during harvesting, storage and transport.

For actual histological diagnosis, the tissue specimen must be separated from the effluent. The smallness of the samples make it very difficult and time consuming to separate and process the samples in the laboratory. Upon separation, it is desirable to immobilize the pieces of tissue within some device such as sponge or in filter paper biopsy bag which resembles tea bag to prevent them from becoming lost during processing.

SUMMARY OF THE INVENTION

The present invention provides a filtration station for capturing small to medium sized tissue fragments in fluid for histological processing. The filtration station allows tissue to be filtered into either foam in a cassette or into a biopsy bag, with speed, excellent tissue recovery and convenient fixative collection for recycling or disposal. The primary feature of the present invention is the combination of two normally separate filtration stations into one station for more convenient filtration of tissue into two widely used filter media while also reducing exposure to harmful vapors. Other novel features of the invention include: (i) combination of two holders for two commonly used filtration media (foam and biopsy bags; (ii) unique holder for using biopsy foam, thereby speeding up use and permitting capture of effluent for recycling; (iii) unique holder for biopsy bags, thereby speeding up use and permitting capture of effluent for recycling; (iv) unique funnel for use with both the foam holder and the biopsy bag holder; and (v) unique features of both media holders and the funnel permit the same funnel to direct specimens into either holder.

In one embodiment of the invention, the present invention provides two separate substations within one structure. The single structure is comprised of a container with a lid. One substation is comprised of a foam funnel cassette well with drainage holes within the lid. The well is sized to hold a standard histology processing cassette. The substation provides for filtration of specimens through a foam pad within the cassette and the container provides a reservoir for the suspending fluids to go into while tissue is being filtered out by the foam pad in the cassette. A funnel is also included to provide a pouring transition means for a sample tissue effluent solution from a specimen container to the foam pad.

The other substation provides a holder for biopsy bags, i.e., small filter bags which resemble tea bags. The holder is comprised of an open cylindrical shape with a bottom integrated with a section of the lid. The lid portion at the bottom of the cylinder is perforated. The cylinder holds the biopsy bags and the funnel holds and seals the biopsy bag during filtration. The drainage holes direct the filtration fluid into the container. The same funnel may be used for either substation.

In another embodiment of the invention, a more compact unit is provided with one substation implemented on one side of the lid and the other substation implemented on the opposite side of the lid.

The present invention provides a faster and more convenient filter separation of samples within an effluent. The present invention also provides a convenient effluent recovery for recycling and disposal purposes. There is also reduced exposure to laboratory personnel to vapors from toxic effluents. The present invention also provides the availability of selecting efficient use of one of two common histology filter types depending on specimen needs in one station using shared tools such as one funnel for both filter types.

These together with other objects of the invention, along with various features of novelty which characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there is illustrated a preferred embodiment of the invention.

DETAILED DESCRIPTION OF THE INVENTION

Figure 1:
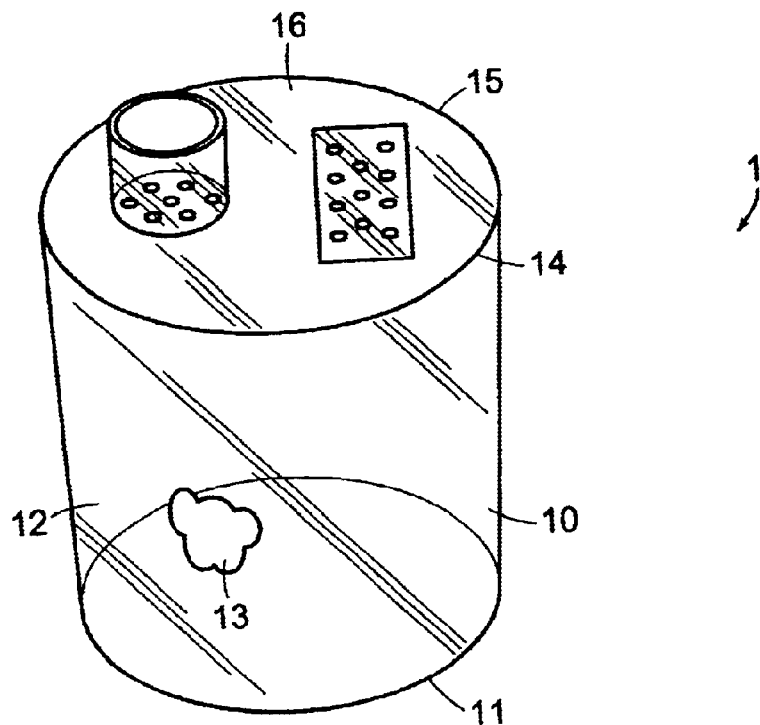
FIG. 1 is a front perspective view of one embodiment of the invention.
Figure 2A:
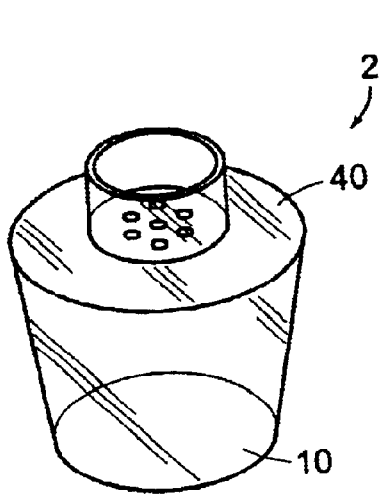
FIGS. 2A and 2B are front perspective views of another embodiment of the invention.
Figure 2B:
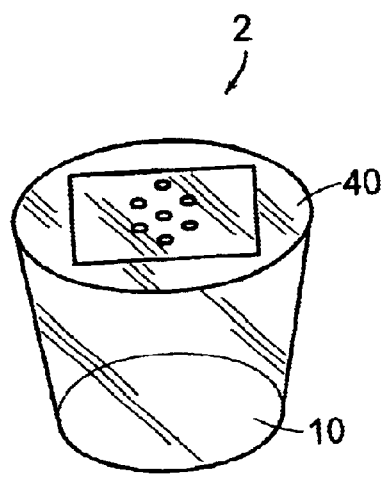
Figure 3:
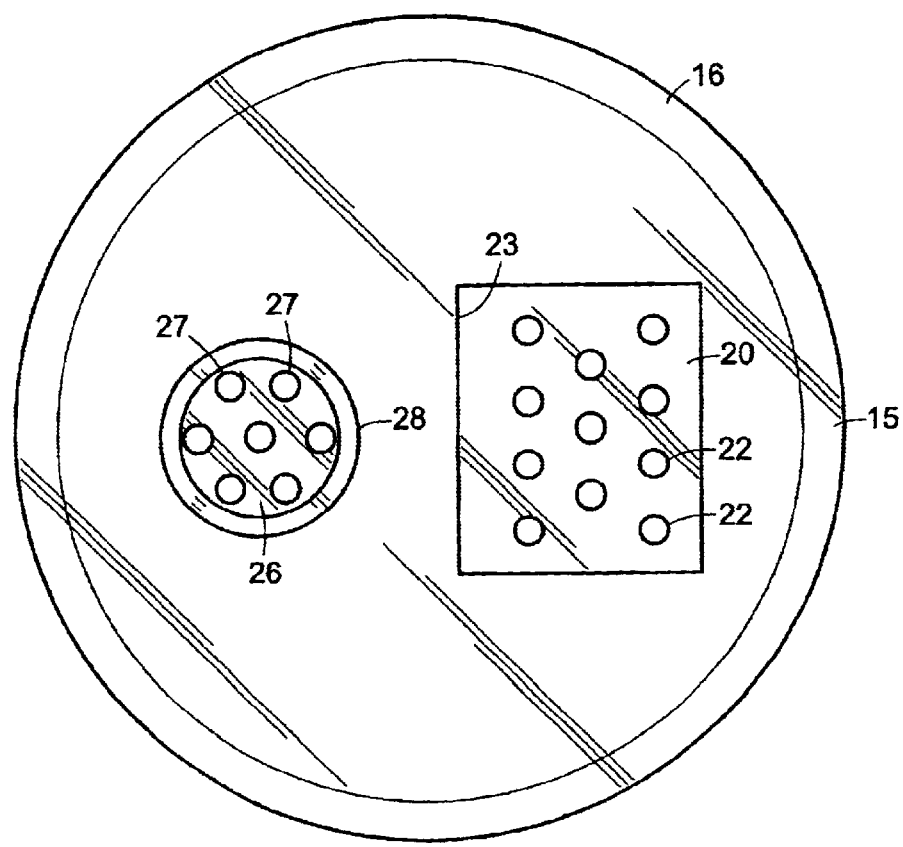
FIG. 3 is a top view of the invention embodiment shown in FIG. 1.
Figure 4:
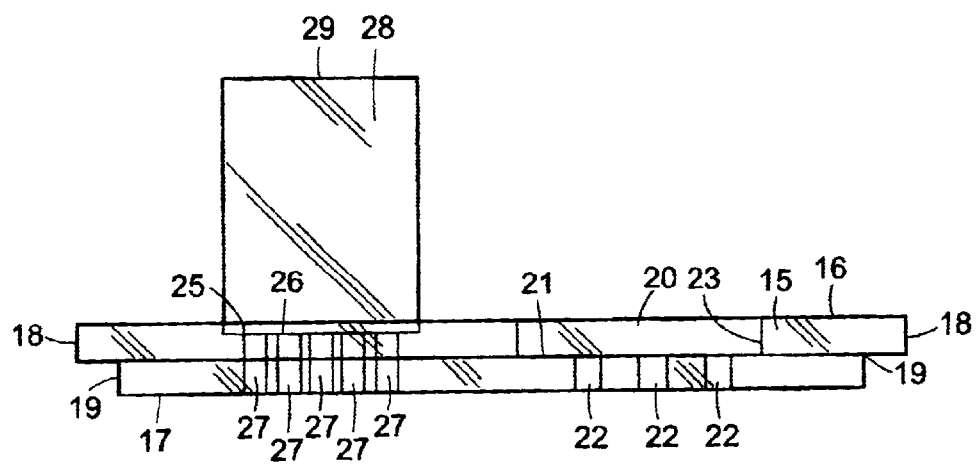
FIG. 4 is a side view of the lid shown in FIG. 3.
Figure 5:
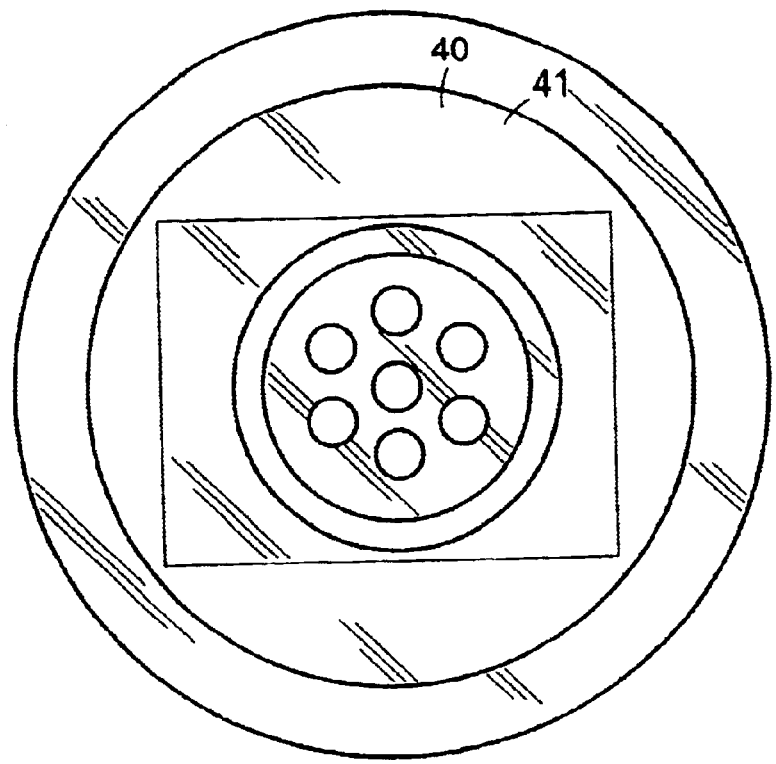
FIG. 5 is a top view of the invention embodiment shown in FIG. 2A.
Figure 6:
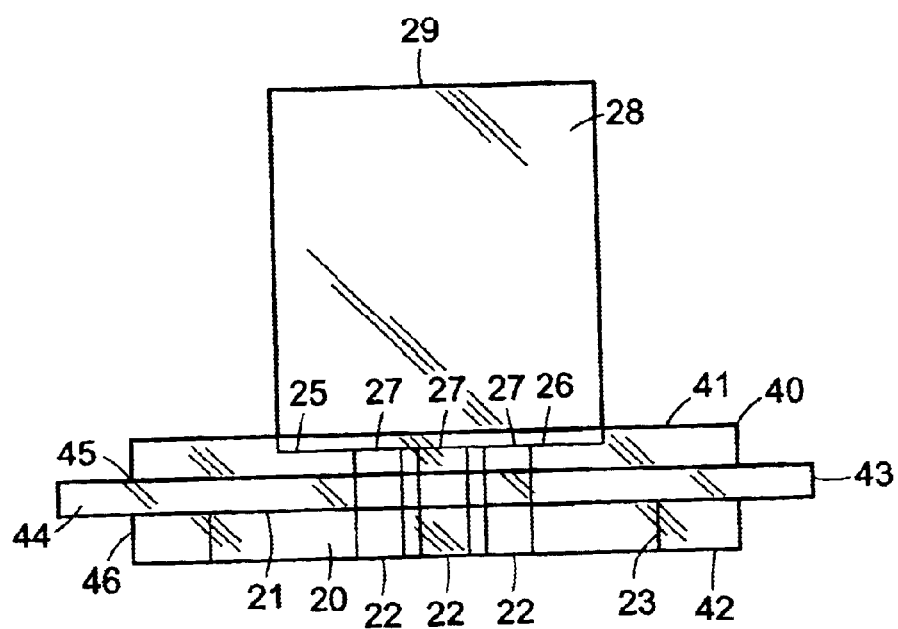
FIG. 6 is a side view of the lid shown in FIG. 5.
Figure 7:
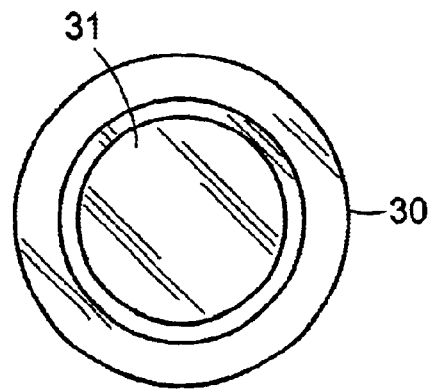
FIG. 7 is a top view of the funnel of the invention.
Figure 8:
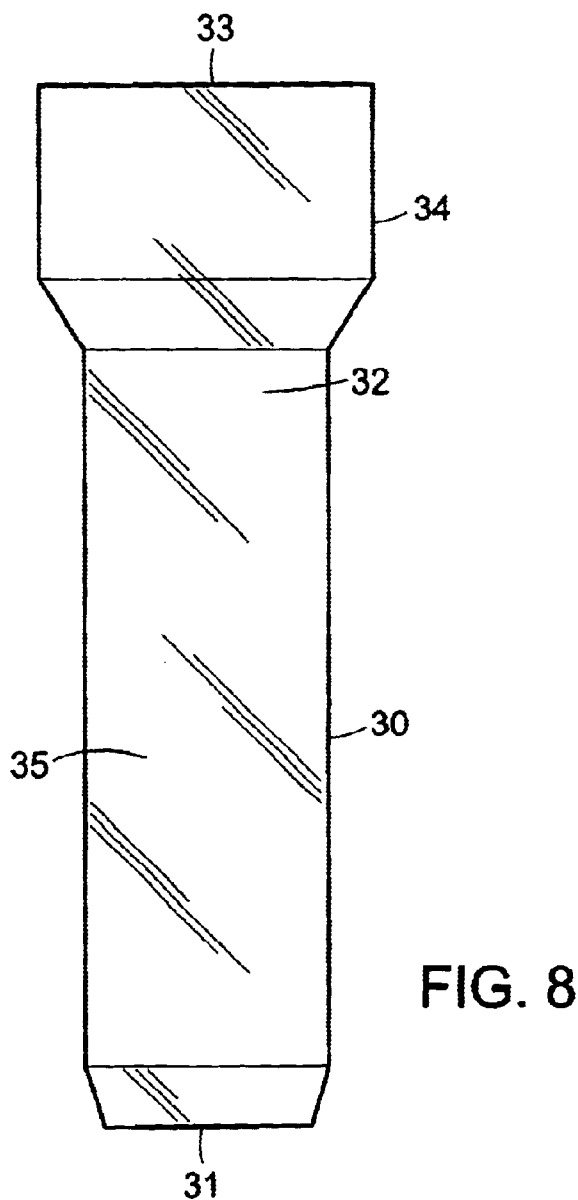
FIG. 8 is a side view of the funnel of FIG. 7.

Referring to the drawings in detail wherein like elements are indicated by like numerals, there is shown in FIG. 1 a biological filtration station embodiment 1 constructed according to the principles of the present invention. The filtration station 1 is comprised of a reservoir container 10 having a bottom 11 from which generally cylindrical side walls 12 extend vertically upward terminating in an open top 14, said container 10 being generally cylindrical in shape, said container 10 having the longitudinal axis generally perpendicular to the container bottom 11, said container 10 having a lid 15 removably attached to said side walls 12 for covering the interior 13 of said container 10.

The lid 15 is round and generally planar having a top surface 16 and a bottom surface 17, said bottom surface 17 enclosing the container interior 13 when the lid 15 affixed to the container top 14. The lid 15 may be made from an acrylic resin such as sold under the trademark, PLEXIGLAS. In this embodiment of the invention the lid 15 has a perimeter 18 with a 90° groove 19 formed therein resulting in the top surface 16 having a larger diameter than the bottom surface 17.

The lid top surface 16 has a generally rectangular cassette well 20 formed therein. The rectangular well 20 is sized to hold a standard histology processing cassette 3. The bottom 21 of the rectangular well 20 has a series of holes 22 formed therein, said holes 22 extending through the lid 15 and opening onto the lid bottom surface 17.

The lid top surface 16 also has a generally round well 25 formed therein. The round well 25 has a bottom 26 from which generally a hollow cylindrical holder 28 extends vertically upward, said cylinder 28 having a longitudinal axis generally perpendicular to the round well bottom 26. The holder 28 has an open top 29. The round well bottom 26 has a series of holes 27 formed therein, said holes 27 extending through the lid 15 and opening onto the lid bottom surface 17.

The filtration station 1 is also comprised of a funnel 30 having an open bottom 31 from which cylindrical main body side walls 32 extend vertically upward, said funnel 30 being generally cylindrical in shape and having a longitudinal axis generally perpendicular to the funnel bottom 31, said funnel side walls 32 terminating in an open funnel top 33. The funnel bottom 31 is beveled inward resulting in a smaller diameter at the funnel bottom 31 then along the side walls 32 of the main body 35. The funnel 30 has an upper portion 34 comprising approximately 25% of the upper longitudinal length of the funnel 30 and terminating at the funnel top 33. The diameter of the upper portion 34 increases approximately 30% over the diameter of the main body 35.

In an alternate embodiment of the invention a filtration station 2 is comprised of a reservoir container 10 having a bottom 11 from which generally cylindrical side walls 12 extend vertically upward, said container 10 being generally cylindrical in shape, said container 10 having the longitudinal axis generally perpendicular to the container bottom 11, said container 10 having a lid 40 removably attached to said side walls 12 for covering the interior 13 of said container 10.

The lid 40 is round and generally planar having a first surface 41 and an opposite second surface 42. The lid 40 may be made from an acrylic resin such as sold under the trademark, PLEXIGLAS. In this embodiment of the invention the lid 40 has a perimeter 43 with central protruding flange 44 forming a first 90° groove 45 and a second 90° groove 46 resulting in the flange 44 having a larger diameter than the either of the surfaces 41, 42.

The lid first surface 41 also has a generally round well 25 formed therein. The round well 25 has a bottom 26 from which generally a hollow cylindrical holder 28 extends vertically upward, said cylinder 28 having a longitudinal axis generally perpendicular to the round well bottom 26. The holder 28 has an open top 29. The round well bottom 26 has a series of holes 27 formed therein, said holes 27 extending through the lid 40 and opening onto the lid second surface 42.

The lid second surface 42 has a generally rectangular cassette well 20 formed therein. The rectangular well 20 is sized to hold a standard histology processing cassette 3. The bottom 21 of the rectangular well 20 has the round well holes 27 opening therein.

The filtration station 2 is also comprised of a funnel 30 having an open bottom 31 from which cylindrical main body side walls 32 extend vertically upward, said funnel 30 being generally cylindrical in shape and having a longitudinal axis generally perpendicular to the funnel bottom 31, said funnel side walls 32 terminating in an open funnel top 33. The funnel bottom 31 is beveled inward resulting in a smaller diameter at the funnel bottom 31 then along the side walls 32 of the main body 35. The funnel 30 has an upper portion 34 comprising approximately 25% of the upper longitudinal length of the funnel 30 and terminating at the funnel top 33. The diameter of the upper portion 34 increases approximately 30% over the diameter of the main body 35.

In operation, the rectangular well 20 in both filter stations 1, 2 is used to hold a standard histology processing cassette 3 with a foam pad 4 and the round well 25 is used for a biopsy bag 5.

The rectangular well 20 provides solid support for the cassette 3 during the filtration process. The rectangular well bottom holes 22 provides free flow of the preservative effluent 7 into the container interior 13. The funnel 30 provides a pouring transition means for a sample tissue effluent solution from a specimen container 6 onto the cassette foam pad 4. The funnel's steep side walls 32 minimizes adhesion of tissue fragments to the side walls 32. The funnel upper portion 34 is large enough to permit pouring directly into the funnel top 33 from specimen containers 6 of approximately 30 to 90 cc's. The funnel 30 is tapered at its bottom 31 thereby ensuring a fit between cassette sides. The tapered funnel bottom 31 also compresses the foam edges forming a seal trapping suspended tissue fragments on the foam pad 4 while the effluent 7 passes through the foam pad 4 and well perforations 22 into the reservoir 13. The rectangular well walls 23 and drainage holes 22 direct the filtration fluid 7 into the container interior 13 preventing spilling over the top surface 16, 41, 42 and perimeter 18, 43 the container lid 15, 40.

The holder 28 provides solid support for biopsy bags 5 during the filtration process. The round well bottom holes 27 provide free flow of effluent 7 into the container interior 13. The funnel 30 provides a pouring transition means for a sample tissue effluent solution from a specimen container 6 into the biopsy bag 5. The tapered funnel bottom 31 is fitted into the holder top 33 thereby locking the biopsy bag 5 in place and preventing biopsy bag collapse. The fit of the well and funnel bottom forms a seal trapping the open portion of the biopsy bag preventing escape of fluid and tissue, as well as preventing the bag from prematurely separating from the funnel. The same funnel 30 may be used for either substation 20, 25.

The second embodiment of the filtration station 2, provides a more compact unit with one substation 20 implemented on one side 42 of the lid 40 and the other substation 25 implemented on the opposite side 41 of the lid 40. The substation 20 or 25 not being used will be on the lid side 42 or 41 covering and facing the container interior 13.

It is understood that the above-described embodiments are merely illustrative of the application. Other embodiments may be readily devised by those skilled in the art which will embody the principles of the invention and fall within the spirit and scope thereof.

We claim:

1. A filtration station for capturing small to medium sized biological tissue fragments in fluid for histological processing, comprising:
   a reservoir container;
   a lid adapted to sealingly engage said container;
   a foam funnel cassette well in said lid with drainage holes through said lid, said well adapted to hold a standard histology processing cassette with a foam pad;
   a funnel connected to said cassette well, said funnel adapted to provide a pouring transition means for a sample tissue effluent solution from a specimen container to the foam pad;

a holder for a filter paper biopsy bag, said holder being comprised of an open cylindrical shape with a bottom integrated with a perforated section of the lid;

wherein said drainage holes and perforations are adapted to direct filtration fluid into the container.

2. A filtration station as recited in claim 1, wherein:

the reservoir container has a bottom from which generally cylindrical side walls extend upward terminating in an open top, said container having a longitudinal axis generally perpendicular to the container bottom, said side walls, bottom and top defining a container interior;

the lid covers said open top and is removably attached to said side walls.

3. A filtration station as recited in claim 2, wherein:

said lid is round and generally planar having a top surface and a bottom surface, said bottom surface enclosing the container interior when the lid is affixed to the container side walls.

4. A filtration station as recited in claim 3, wherein:

said cassette well is formed in the lid top surface, said well having a bottom with a series of drainage holes formed therein, said holes extending through the lid and opening onto the lid bottom surface.

5. A filtration station as recited in claim 4, wherein:

a second, a generally round well formed therein, said round well having a bottom with a series of holes formed therein, said holes extending through the lid and opening onto the lid bottom surface;

said holder is generally hollow and cylindrical, extending vertically upward to an open top, said cylinder having a longitudinal axis generally perpendicular to the round well bottom.

6. A filtration station as recited in claim 5, wherein:

the funnel has an open bottom from which cylindrical main body side walls extend vertically upward, said funnel being generally cylindrical in shape and having a longitudinal axis generally perpendicular to the funnel bottom, said funnel side walls terminating in an open funnel top.

7. A filtration station as recited in claim 6, further comprising:

a cassette with a foam pad positioned within said cassette well.

8. A filtration station as recited in claim 7, wherein:

said funnel bottom is beveled inward.

9. A filtration station for capturing small to medium sized biological tissue fragments in fluid for histological processing, comprising:

a reservoir container having a bottom from which generally cylindrical side walls extend vertically upward to an open top, said bottom, side walls and top defining an interior, said container being generally cylindrical in shape, said container having the longitudinal axis generally perpendicular to the container bottom;

a lid removably attached to said side walls for covering the interior of said container, said lid being round and generally planar having a first surface and an opposite second surface;

a generally round well formed in the lid first surface, said well having a bottom having a series of holes formed therein, said holes extending through the lid and opening onto the lid second surface;

a hollow cylindrical holder for a filter paper biopsy bag extending vertically upward from said round well, said cylinder having a longitudinal axis generally perpendicular to the round well bottom, said holder having an open top;

a generally rectangular cassette well formed in the lid second surface, said rectangular well being sized to hold a standard histology processing cassette, said having a bottom having the round well holes opening therein.

10. A filtration station as recited in claim 9, further comprising:

a funnel having an open bottom from which cylindrical main body side walls extend vertically upward, said funnel being generally cylindrical in shape and having a longitudinal axis generally perpendicular to the funnel bottom, said funnel side walls terminating in an open funnel top.

11. A filtration station as recited in claim 10, further comprising:

a cassette with a foam pad positioned within said cassette well.

12. A filtration station as recited in claim 11, wherein:

said funnel bottom is beveled inward.

* * * * *